United States Patent [19]
Tadion

[11] Patent Number: 5,928,680
[45] Date of Patent: Jul. 27, 1999

[54] APPARATUS FOR MAKING SAMPLES FOR INFRARED ANALYSIS

[76] Inventor: Jay Tadion, 75 Avenue General Guisan, 1009-Pully/Lausanne, Switzerland

[21] Appl. No.: 08/917,837
[22] Filed: Aug. 27, 1997
[30] Foreign Application Priority Data Aug. 27, 1996 [GB] United Kingdom .................. 9617817

[51] Int. Cl.$^6$ ............................ B29C 43/56; B29C 43/02
[52] U.S. Cl. ........................................ 425/405.1; 425/420
[58] Field of Search ................................ 425/405.1, 420, 425/412

[56] References Cited

U.S. PATENT DOCUMENTS

| 3,794,458 | 2/1974 | Iwasaki | 425/405.1 |
| 4,054,405 | 10/1977 | Facey et al. | 425/405.1 |
| 4,534,721 | 8/1985 | Iwasaki et al. | |
| 4,732,556 | 3/1988 | Chaing et al. | 425/405.2 |

FOREIGN PATENT DOCUMENTS

| 319002 | of 1931 | United Kingdom . |
| 767532 | 2/1957 | United Kingdom . |
| WO 81/03304 | 11/1981 | WIPO . |

*Primary Examiner*—Mary Lynn Theisen
*Attorney, Agent, or Firm*—Everett G. Diederiks, Jr.

[57] ABSTRACT

An evacuable KBr die includes a base, a cylindrical barrel, a pellet arranged in a bore of the barrel, a piston which also fits within the bore, and an evacuable pad. O-rings are provided to create seals between the various components. Sample material for analysis is pressed between the piston and the pellet while a vacuum is created at the top and bottom of the sample to remove water vapor from the sample. For this purpose, passages are provided in both the base and barrel to transmit the vacuum from the pad to the upper and lower ends of the bore.

18 Claims, 1 Drawing Sheet

5,928,680

APPARATUS FOR MAKING SAMPLES FOR INFRARED ANALYSIS

BACKGROUND OF THE INVENTION

Field of the Invention

This invention relates to apparatus for making samples for use in infrared or other spectropscopic analysis.

An evacuable KBr (potassium bromide) die is extensively used in infrared analysis. In this die, a sinterable infrared transmitting powder, usually potassium bromide or potassium chloride, mixed with the sample under investigation, is pressed typically at a load of about 30 tons per square inch to produce a disc or pellet. This is effected under vacuum so as to help remove water from the sample and to reduce fogging. The disc is then placed in the appropriate instrument for analysis.

In the known method of producing such a disc described above, the mixture of sample and substrate powder is placed between two pellets and a piston is used to apply force to one of the pellets in order to apply the compressive load. On one side of the die is an evacuation outlet which is used to evacuate the die during compression. This is done in order to reduce the amount of water in the disc to avoid the results of the infrared analysis from being contaminated by the absorption bands or water.

SUMMARY OF THE INVENTION

According to a first aspect of the present invention there is provided a die for making samples for infrared or other analysis, said die comprising a base, a barrel arranged on said base and having a bore receiving a pressing piston, said die having a space for receiving powder to be pressed, and having passage means for evacuating said powder receiving space from respective ends thereof.

Thus in accordance with the present invention the powder disc can be evacuated from both sides, rather than from just one side as has been the case up to now. This has been found to be considerably more effective in removing water from the sample disc than if evacuation is carried out from one side only, and produces a higher quality disc for analysis.

The base and the barrel are provided with suitable evacuating passages. Although separate vacuum sources could be connected to the respective die parts, preferably for ease of use, a single vacuum connection is provided. Preferably, therefore, the base part and barrel are provided with connecting passages for transmission of the vacuum from one part to the other.

One or other die part may be provided with a vacuum connection port to which a vacuum source may be coupled. Preferably, however, the die comprises a separate evacuable base member to which a vacuum connection may be made and upon which the other die parts stand. A vacuum pipe or the like may then be permanently attached to the base member and the die placed on the member as and when necessary. This is a convenient arrangement since it obviates the frequent connection and disconnection of vacuum pipes from the die as is required with known dies. It also means that different dies could be positioned on a common base, thereby reducing the need for separate vacuum attachments being provided on individual dies.

Such an arrangement is believed to be novel and advantageous in itself and is applicable not only to dies described above having evacuation of a sample from both sides, but also to conventional dies which evacuate from a single position. Thus from a second aspect the present invention provides a die for making samples for infrared or other analysis, said die comprising opposed sample forming parts and a separate evacuation member having vacuum attachment means upon which said sample forming parts are mounted in use.

Suitable sealing means such as an O ring may be arranged between the evacuation member and the other die parts.

In conventional die constructions, the sample powder is compressed between two pellets. The piston acts on an upper pellet and the lower pellet is received on a suitable base. The powder contacting face of each pellet is polished precisely to produce a sample disc having surfaces which are optically flat. However, in a preferred embodiment of the present invention, the upper pellet is dispensed with and the sample disc is formed in the bore of the barrel between the lower end of the piston and the upper surface of a single pellet. The powder contacting face of the piston is formed in a suitable manner, e.g. polished, to produce a suitable finish on the sample disc. This arrangement has the advantage of reducing the number of components required to use the die, and furthermore means that more powder may be added to discs being formed merely by removing the pressing piston and adding more powder, which previously would have required dismantlement of the whole die.

Using the pressing piston to form a disc directly is novel and advantageous in itself, not just in the context of the particular die constructions described above. Thus from a further aspect the invention provides a die for making samples for infrared or other analysis comprising a barrel having a bore receiving a piston and a single pellet, the sample being formed directly between the piston and the pellet.

The pellet may be formed as an integral part of the base but preferably it is a separate component which rests on the surface of the base part. Preferably a space is defined between the base part and the barrel which transmits a vacuum to the periphery of the pellet, to allow evacuation of the powder receiving chamber from below. Accordingly, the pellet is preferably sized such as to be a close fit within the barrel bore so as to prevent extrusion of the sample around the sides thereof, but still allow a vacuum to be drawn around its sides. Typically a clearance of about 0.005 mm may be provided for this purpose.

In the preferred embodiment, a passage extends from said gap through the wall of said barrel to open into the barrel bore above the lower end of the piston so as to transmit a vacuum to the periphery thereof. Again, the lower end of the piston is sized similarly to the pellet so as to prevent extrusion of the sample around the sides thereof, but to allow a vacuum to be drawn from the sample during pressing.

The upper end of the pressing piston may be of a smaller diameter than the sample contacting end, so that it may fit more easily within the barrel bore and be used to tamp down powder during filling of the die.

Once a sample disc is formed, it must be pressed out of the die, usually by the pressing piston. For such purpose, a separate ring is usually provided over which the die is placed and into which the sample is pressed. In accordance with a preferred feature of the invention, the base part of the die may be formed on its underside with a cavity having a diameter greater than that of the sample being formed, and into which the sample may be pressed for removal and use. Thus after a sample has been pressed, the base is inverted, the barrel placed on the base over the cavity and the sample then pressed out into the cavity. This obviates the need for a separate component which may inadvertently be lost during use. This is applicable not only in the particular die constructions defined above, but also in other sample dies, so from a further aspect, the invention provides a die for making a sample for infrared or other analysis, comprising a base and a barrel arranged removably on said base and having a bore for forming said sample and receiving a pressing piston, the base having a cavity into which said sample may be extracted after formation.

In the preferred embodiment described the base cavity is positioned over an opening in an upper surface of the separate evacuation member and the base comprises a passage leading from the cavity to the gap between the base and the barrel for transmission of the vacuum thereto.

BRIEF DESCRIPTION OF THE DRAWING

A preferred embodiment of the invention will now be described with reference to the accompanying FIG. 1 which shows a schematic cross section of a die in accordance with the invention.

DETAILED DESCRIPTION OF THE PREFERRED EMBODIMENT

Figure 1:
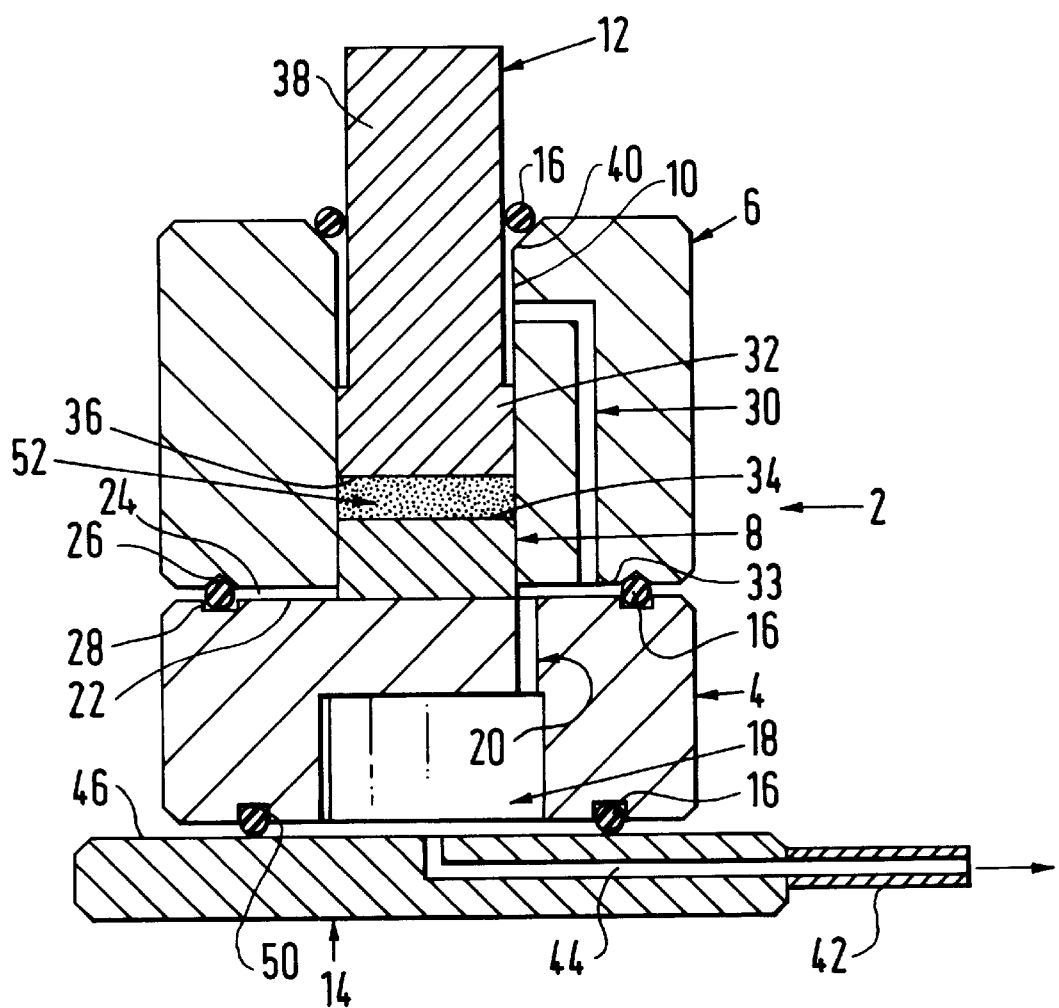

With reference to the Figure, a die 2 embodying the invention 2 comprises five main components, namely a base 4, a cylindrical barrel 6, a pellet 8 arranged in a bore 10 of the barrel 6, a piston 12 which also fits within the bore 10, and an evacuable pad 14. O rings 16 are provided as shown to seal between the various components.

Turning to the individual components, the base 4 is a cylindrical block of a material such as stainless steel which has a cylindrical cavity 18 provided in its underside, for a purpose to be described below. A passage 20 leads from the base of the cavity 18 to the upper surface 22 of the base 4.

The barrel 6 is positioned on the base 4 with an O ring seal 16 as shown to define a gap 24 therebetween. The barrel 6 has an annular V groove 26, and the base upper surface 22 a rectangular section groove 28 to locate the O ring 16.

The wall of the barrel 6 is provided, eg drilled, with an L shaped passage 30 which extends between the lower end 33 of the barrel 6 and the bore 10. As can be seen, the passages 20, 30 in the base 4 and barrel 6 respectively are in fluid communication through the gap 24.

The bore 10 of the barrel 6 accommodates the pellet 8 which in use rests on the upper surface 22 of the base 4. The pellet 8 is circular in section and is sized to fit closely within the bore 10. A clearance of about 0.005 mm may be provided. This is sufficiently small to prevent extrusion of material around the pellet 8 during pressing, but permits a vacuum to be drawn around the side of the pellet as will be described further below. The upper surface 34 of the pellet 8 is preferably polished to produce a suitable optical finish on the pressed sample.

The piston 12 also fits within the bore 10 and is in the form of a cylindrical rod. The lower end 32 of the piston 12 has a diameter substantially similar to that of the pellet 8, again to prevent extrusion around the piston 12 and to allow a vacuum to be drawn around the piston 12. The lower face 36 of the piston 12 is also preferably polished to provide a suitable optical finish on the pressed sample. The upper end 38 of the piston 12 is of a smaller diameter, for example with a clearance of about 0.05 mm, and this can be used to act as a tamper to tamp down powder during filling of the die. The upper end of the bore 10 has a chamfer 40 for receiving a further O ring 16 through which the piston 12 slides. This acts as a vacuum seal at the upper end of the bore 10.

The evacuable pad 14 is relatively thin and comprises a vacuum pipe fitting 42 for attachment to a vacuum source. A passage 44 leads from the fitting 42 to open onto the upper surface 46 of the pad 14 into the cavity 18 of the base 4. The pad 14 may be permanently fixed to the platen of a press independently of the other parts of the die and could possibly be used with a range of die parts.

The base 4 has a groove 50 for receiving an O ring 16 which seals the gap between the base and the pad 14 in use.

In use, the barrel 6 is positioned on the base 4, with the pellet 8 in the base of the barrel bore 10. An appropriate amount of powder 52 is then poured into the bore 10 and tamped down using the narrow end 36 of the piston 12. The piston is then inverted, and positioned in the bore 10 through the O ring 16. A powder receiving space is thus defined in the bore between the lower face 36 of the piston 12 and the upper surface 34 of the pellet 8. The assembly is then placed on the pad 14 so that the cavity 18 in the base 4 overlies the opening of passage 44.

The piston 14 may then by pressed in a suitable press, and a vacuum drawn through the pad fitting 42. The vacuum will be applied to the lower end of the powder receiving space via the passage 20 in the base, the gap between the base 4 and the barrel 6 and around the side of the pellet 8. A vacuum will also be applied to the upper face of the powder receiving space through the passage 30 in the wall of barrel 6 and around the side of the piston 12.

Once the pressing has been completed, the base 4 and barrel 6 can be removed from the pad 14, and the base 4 inverted. The barrel 6 can then be placed back on the base 4 over the base cavity 18 and the pressed disc pressed out into the cavity for removal and use.

From the above, it will be seen that the described die has a number of significant advantages over the prior art. It allows evacuation of the sample powder for both ends, rather than just one end which improves the quality of the sample. Further, by using the piston to press directly on the powder, it obviates the need for a second pellet, thereby reducing the total number of parts in the die and improving ease of handling. Also, the use of a separate evacuable stand obviates the need for frequent connection and disconnection of a vacuum removal line from the die. Finally, by incorporating a cavity in the die base, the need for a separate extrusion ring is obviated, adding to the ease of using the die. All these advantageous features are believed to be inventive in their own right, and may be applied in dies not limited to the double ended evacuation arrangement disclosed in the preferred embodiment.

Of course various modifications may be made to the preferred embodiment described above without departing from the scope of the invention. For example the evacuating passage 30 provided in the barrel 6 need not be "L" shaped but could be a straight passage, suitably angled from the lower end 33 of the barrel 6 to open into the bore 10.

I claim:

1. A die for making samples for infrared or other analysis, said die comprising a bases a barrel having a bore arranged on said base and for receiving a pressing piston, said die having a chamber for receiving powder to be compressed, and having passage means for evacuating said chamber from respective ends thereof.

2. A die as claimed in claim 1 wherein said base part and barrel are provided with connecting passages for transmission of a vacuum from one part to the other.

3. A die as claimed in claim 1 comprising a single connector for connection to an external vacuum supply.

4. A die as claimed in claim 1 comprising a separate evacuation member which receives and which transmits the vacuum to the base.

5. A die as claimed in claim 1 wherein the powder receiving chamber is defined in a bore of said barrel between the upper surface of a pellet and the lower end of the pressing piston.

6. A die as claimed in claim 1 wherein a space is defined between the base part and the barrel for transmitting a vacuum to the lower end of the powder receiving chamber.

7. A die as claimed in claim 6 wherein a pellet forming the bottom of the powder receiving chamber rests on the base part and the vacuum is transmitted to the periphery of the pellet.

8. A die as claimed in claim 6 wherein said barrel comprises a passage which extends from said gap through the wall of said barrel to open into the barrel bore above the lower end of the piston for transmitting a vacuum to the periphery thereof.

9. A die as claimed in claim 1 wherein the lower end of said piston is polished.

10. A die as claimed in claim 1 wherein the upper end of the pressing piston is of a smaller diameter than the lower end.

11. A die as claimed in claim 1 wherein the base of the die is formed on its underside with a cavity into which the sample may be extracted after formation.

12. A die for making samples for infrared or other analysis, said die comprising a base, a barrel having a bore arranged on said base and for receiving a pressing piston, a pellet arranged in said bore and supported by said base, the bottom of the piston and the upper surface of the pellet defining in the bore a chamber receiving powder to be compressed, said die further comprising an evacuable member supporting said base, and passage means provided in said base and said barrel to transmit a vacuum to the upper and lower ends of said chamber respectively.

13. A die as claimed in claim 12 wherein a space is defined between the base and the barrel for transmitting a vacuum to the lower end of the pellet, and a passage is formed in said barrel which extends from said space through the wall of said barrel to open into the barrel bore.

14. A die as claimed in claim 13 wherein said base has a cavity formed on its underside and said evacuable member has a vacuum transmitting passage provided on its upper surface, said cavity overlying said vacuum transmitting passage, said base having a further passage extending from said cavity to its upper surface for transmitting a vacuum to the space between the base ad the barrel.

15. A die for making a sample for infrared or other analysis, comprising a base and a barrel arranged removably on said base and having a bore in which said sample is formed, and receiving a pressing piston, said base having a cavity into which said sample may be pressed after its formation.

16. A die for making samples for infrared or other analysis, said die comprising opposed sample forming parts and a separate evacuation member having vacuum attachment means and upon which said sample forming parts are positioned in use.

17. A die for making samples for infrared or other analysis comprising a barrel having a bore receiving a piston and a single pellet, the sample being formed directly between the piston and the pellet.

18. A die as claimed in claim 7 wherein said barrel comprises a passage which extends from said gap through the wall of said barrel to open into the barrel bore above the lower end of the piston for transmitting a vacuum to the periphery thereof.

\* \* \* \* \*